United States Patent
Poole

[11] 3,948,746
[45] Apr. 6, 1976

[54] DISSOLVED OXYGEN PROBE

[75] Inventor: Robert L. Poole, Willow Grove, Pa.

[73] Assignee: Fischer & Porter Co., Warminster, Pa.

[22] Filed: Jan. 20, 1975

[21] Appl. No.: 542,678

[52] U.S. Cl. .............................. 204/195 P; 324/29
[51] Int. Cl.² ....................................... G01N 27/46
[58] Field of Search ............ 204/1 T, 195 P, 195 R

[56] References Cited
UNITED STATES PATENTS

| | | | |
|---|---|---|---|
| 2,913,386 | 11/1959 | Clark | 204/195 P |
| 2,943,028 | 6/1960 | Thayer et al. | 204/195 R |
| 3,088,905 | 5/1963 | Glover | 204/195 P |
| 3,351,544 | 11/1967 | Medlar | 204/195 P |
| 3,510,421 | 5/1970 | Gealt | 204/195 P |
| 3,515,658 | 6/1970 | Amdur | 204/195 P |
| 3,577,332 | 5/1971 | Porter et al. | 204/195 P |
| 3,703,457 | 11/1972 | Niedrach et al. | 204/195 P |

*Primary Examiner*—T. Tung

[57] ABSTRACT

A probe immersible in liquid having oxygen dissolved therein and adapted to continuously and accurately measure the oxygen concentration. The probe includes a noble metal measuring electrode, a copper counter-electrode and a potassium hydroxide electrolyte which together define a galvanic cell whose output current depends on the amount of oxygen passing into the cell through a diffusion membrane permeable only to gases. The oxygen within the cell is electrochemically reduced at the surface of the measuring electrode to generate a current that is proportional to the oxygen concentration, the counter-electrode being oxidized.

7 Claims, 3 Drawing Figures

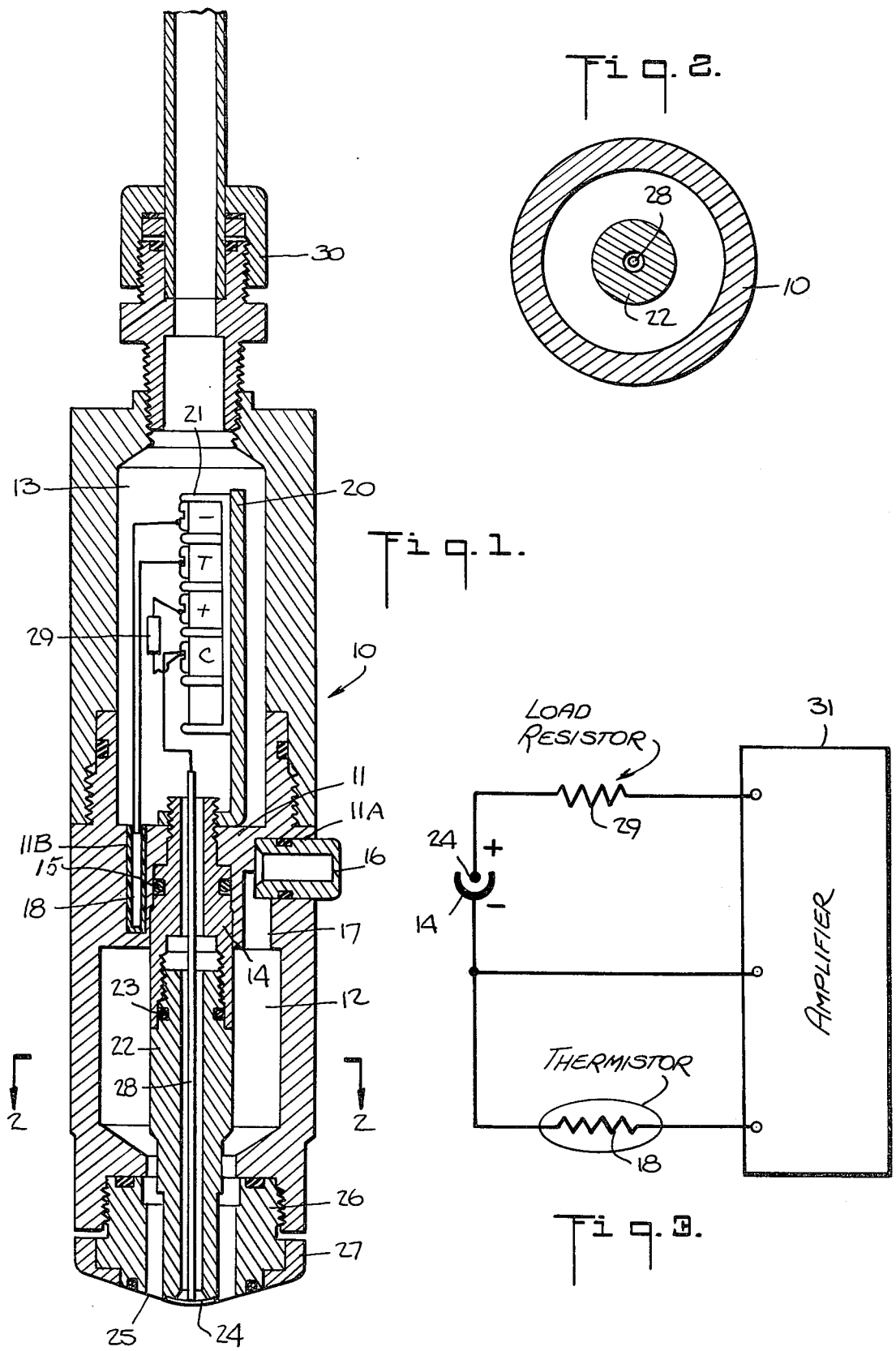

DISSOLVED OXYGEN PROBE

BACKGROUND OF INVENTION

This invention relates generally to the electrochemical analysis of oxygen, and more particularly to a submersible probe adapted to continuously analyze the concentration of oxygen dissolved in a liquid.

In liquid wastes, the factor which determines whether biological changes are being brought about by aerobic or by anaerobic organisms is dissolved oxygen. Aerobic activity requires free oxygen and produces innocuous end products, whereas anaerobic activity can utilize chemically bonded oxygen such as sulfates to produce end products which are obnoxious. Because both types are ubiquitous in nature, it is vital in waste treatment that conditions conducive to aerobic activity be encouraged, for otherwise anaerobic organisms will take over.

Thus in aerobic treatment processes intended to purify sewage and industrial wastes, the present practice is to continuously measure the dissolved oxygen in order to monitor and maintain proper aerobic conditions. Since all aerobic treatment techniques depend upon the presence of dissolved oxygen, the continuous testing thereof is essential when regulating the rate of aeration, not only to insure that the supply of oxygen is adequate to maintain aerobic conditions, but also to prevent excessive use of energy needed for aeration.

The need for dissolved oxygen measurement is by no means limited to sanitary engineering, for oxygen is a significant factor in iron and steel corrosion, such as in steam boilers. Thus in control systems for removing oxygen from boiler-feed waters, it is customary in the power industry to measure the dissolved oxygen concentration.

Dissolved oxygen probes of the electrochemical type are well known. Some of these probes exploit the magnitude of the depolarizing effect of oxygen on a special galvanic cell. Thus in U.S. Pat. Nos. 3,510,421 and 3,239,444 there are disclosed embodiments of electrochemical cells which are immersible in liquid for measuring the concentration of dissolved oxygen. In its simplest form, the cell is constituted by an anode and a cathode bridged by an electrolyte. The cell is adapted by means of a diffusion membrane permeable only to gases but impermeable to liquids to receive a sample of oxygen. Upon the entry of the sample, a chemical reaction occurs, modifying the electrical characteristics of the cell.

In U.S. Pat. No. 3,239,444, the consumable anode is fabricated of cadmium and the inert cathode is of gold, the electrolyte being an aqueous solution of sodium chloride. The elctrochemical reaction in this cell produces cadmium hydroxide which, as pointed out in this patent, is only soluble to a slight extent and appears on the anode as a deposit which increases the electrical resistance of the cell. As a consequence, the cell after a period of time becomes ineffective and the deposit must be removed in order to again render the cell operative.

U.S. Pat. No. 3,510,421 also recognizes that the electrochemical cell disclosed therein for measuring dissolved-oxygen is subject to a loss of output current over an extended period of time, this being due to the build-up of particles formed from insoluble precipitates within the electrolyte which eventually limit the flow of output current. The reduced cell output causes the cell to lose its calibration and to, in time, become altogether inoperative. In order to overcome this drawback, the patent provides a filter to trap the insoluble particles. Though a filter will act to prolong the effective life of the cell, in time the filter becomes clogged and the operation of the cell is impaired.

Thus known types of submersible electrochemical cells for measuring dissolved oxygen give rise to serious practical difficulties when used continuously as sensors in waste treatment and other systems in which a control function is carried out, for the loss of accuracy which occurs with the build-up of insoluble precipitates is disturbing to the proper operation of the system. While this can be avoided by frequent cleaning of the cells, this requires that the system be periodically shut down for this purpose.

SUMMARY OF INVENTION

In view of the foregoing, the main object of this invention is to provide an improved probe immersible in a liquid and adapted to carry out a continuous "in situ" analysis of oxygen dissolved therein.

More particularly, an object of this invention is to provide a probe which incorporates a galvanic cell whose output current is proportional to dissolved oxygen, the cell operating reliably and accurately for a prolonged period without the need for cleaning or other maintenance.

Among the significant features of the invention are that it makes use of a low-cost, consumable counter-electrode and that the formation of insoluble precipitates in the cell is minimized so that the effective life of the cell is not impaired.

Also an object of the invention is to provide a highly sensitive, dissolved oxygen probe which includes a temperature sensor to correct the readings for changes in the temperature of the liquid being tested.

Briefly stated, these objects are attained in a probe having a hollow cylindrical casing of insulating material divided into a lower electrolyte chamber and an upper terminal chamber. Mounted on the stem coaxially disposed within the electrolyte chamber is a tubular-shaped copper counter-electrode which is extended into the terminal chamber for electrical connection, the lower end of the electrolyte chamber being closed by a diffusion membrane which covers a measuring electrode and separates the cell from external liquid, the membrane being permeable to dissolved oxygen in the liquid in which the probe is immersed.

Mounted on the end of the stem in the electrolyte chamber is a measuring electrode of gold or platinum, this electrode being connected to a terminal contact in the terminal chamber. The electrolyte chamber is filled with a solution of potassium hydroxide, so that when dissolved oxygen diffuses through the membrane, it is electrochemically reduced at the surface of the measuring electrode to generate a current proportional to the oxygen concentration. The copper counterelectrode is oxidized to complete the cell reaction.

OUTLINE OF DRAWINGS

For a better understanding of the invention as well as other objects and further features thereof, reference is made to the following detailed description to be read in conjunction with the accompanying drawings, wherein:

FIG. 1 is a longitudinal section taken through a dissolved oxygen probe in accordance with the invention.

FIG. 2 is a transverse section taken in the plane indicated by line 2—2 in FIG. 1; and FIG. 3 is a schematic diagram of the probe circuit.

DESCRIPTION OF INVENTION

Referring now to the drawing, there is illustrated in FIG. 1 a preferred embodiment of a dissolved oxygen probe in accordance with the invention, the probe including an oxygenresponsive galvanic cell disposed within a hollow cylindrical casing 10. Casing 10 is fabricated of a suitable electricalinsulating material having good structural strength, such as polyvinyl chloride or polycarbonate. Formed at about the midpoint of the casing in a constriction 11 of reduced internal diameter that effectively divides the interior into a lower electrolyte chamber 12 and an upper terminal chamber 13.

Received within constriction 11 and extending into electrolyte chamber 12 is a tubular anode 14 formed of copper. An O-ring 15 is provided which surrounds anode 14 at its interface with constriction 11 to prevent the leakage of electrolyte from the electrolyte chamber 12 into terminal chamber 13. Inserted within a fill hole 11A formed on one side of the casing at the constriction position is a removable cap 16. The fill hole communicates with a duct 17 leading to the electrolyte chamber, so that the chamber may be filled with a potassium hydroxide solution. Since the cap is submerged when the probe is immersed in the liquid being tested for dissolved oxygen, the cap is provided with an O-ring to prevent leakage.

At a position diametrically opposed to fill hole 11A in cavity 11B within which is supported thermistor 18 that is protectively covered with a moldable plastic such as silastic or RTV.

The upper end of anode 14 projects into terminal chamber 13, the foot of an L-shaped conductive bracket 20 being attached thereto. The leg of the bracket extends upwardly into terminal chamber 13 and supports a terminal contact strip 21 whose - terminal contact is connected to the bracket, thereby providing an output terminal for copper anode 14.

Supported coaxially within the electrolyte chamber is a tubular stem 22 whose upper end is socketed within the lower end of tubular anode 14 and sealed thereto by an "O" ring 23. The lower end of stem 22 protrudes beyond the electrolyte chamber 12. The tip of the stem having a button-shaped measuring electrode 24 mounted thereon. The measuring electrode or cathode is formed of a noble metal such as gold or platinum. Thus the copper anode, the gold or platinum cathode and the potassium hydroxide electrolyte which bridges these electrodes together define a galvanic cell generating a voltage across an output resistor connected to the electrodes. The voltage developed across the resistor depends on the current flow through the cell and this in turn, as will be later explained, is a function of the dissolved oxygen concentration.

Electrolyte chamber 12 is enclosed by a diffusion membrane 25 which covers measuring electrode 24. Membrane 25 is impermeable to liquid but permeable to gases so that dissolved oxygen diffuses into the electrolyte chamber. The gas-permeable membrane may be made of suitable materials such as fluorinated ethylene propylene, Teflon or polyethylene. To stretch this membrane across the measuring electrode, its margin is clamped between an inner membrane retainer 26 which is threadably received within the lower end of the casing and an outer retainer bezel 27 pressed over the inner retainer.

The measuring electrode or cathode 24 is connected by a lead 28 passing through hollow stem 22 into terminal chamber 13 where it is connected to the contact terminal "C," this stem being partially filled with epoxy. Thermistor 18 is connected by leads going into the terminal chamber to terminal contacts "T" and "—". Thermistor 18 is subjected to the same temperature that exists at the membrane. The thermistor serves, as shown in the circuit in FIG. 3, as a temperature-sensitive variable resistor in a feedback voltage path to compensate for the effect of temperature on the dissolved oxygen reading and also to convert the current output of the probe to a detectable voltage.

A load resistor 29 is connected from terminal C to terminal T. The function of resistor 29 is to provide a small but necessary load to the cell. The current output of the cell is applied via a cable connector 30 and a signal cable to a remotely mounted amplifier 31 adapted to convert the current output of the cell to a useful temperature-compensated electronic signal whose value depends solely on the dissolved oxygen concentration. Thus the cell, the load resistor and the thermistor are all housed within the casing.

When dissolved oxygen diffuses through membrane 25, it is electrochemically reduced at the surface of measuring electrode 24 to generate current that is a function of the oxygen concentration in the sample. The copper counter-electrode 14 is oxidized to complete the cell reaction. The chemical actions at the electrodes is expressed by the following equations:

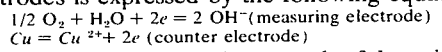

$1/2\ O_2 + H_2O + 2e = 2\ OH^-$ (measuring electrode)
$Cu = Cu^{2+} + 2e$ (counter electrode)

The copper ions formed as a result of the oxidation of the copper counter-electrode react with the hydroxide ions to produce copper-hydroxide complexes or copper oxide which adheres strongly to the copper anode without forming a precipitate that clogs the cell and without significantly reducing current flow. It is to be noted that the hydroxide ions are replenished as a result of oxygen reduction at the measuring electrode.

While there has been shown and described a preferred embodiment of a dissolved oxygen probe, it will be appreciated that many changes and modifications may be made therein without, however, departing from the essential spirit thereof.

I claim:

1. An immersible probe for continuously measuring the concentration of oxygen dissolved in a liquid, said probe comprising:
   A. a tubular insulating casing having an electrolyte chamber whose open mouth is at the lower end of the casing, said chamber having an insulating stem coaxially disposed therein,
   B. a noble metal measuring electrode mounted at the tip of said stem adjacent the mouth of said electrolyte chamber,
   C. a diffusing membrane permeable to oxygen, said membrane closing the mouth of said electrolyte chamber and covering said measuring electrode, and
   D. a tubular copper counter-electrode whose lower end encircles the other end of said stem and lies within said chamber, the upper end of said counter-electrode projecting outside said chamber and being connected to a first terminal, a connection between said measuring electrode and a second terminal external to said chamber being effected by a lead passing through said stem and said tubular counter-electrode, said chamber being filled with an aqueous solution of potassium hydroxide to bridge said electrodes to form an oxygen-sensitive galvanic cell generating a current proportional to the concentration of oxygen diffusing through said membrane, the copper counter-electrode reacting with hydroxide ions to produce copper oxide which adheres to the copper without forming a precipitate that would otherwise clog said cell.

2. A probe as set forth in claim 1, wherein said casing is divided by a constriction into said electrolyte chamber and an upper terminal chamber having a terminal strip therein which includes said first and second terminal connected to said electrodes.

3. A probe as set forth in claim 2, wherein the lower end of said tubular casing is internally threaded and the margin of said membrane is clamped between an internal retainer member threadably received in the lower end of the casing and an outer retainer bezel pressed over the internal member.

4. A probe set forth in claim 2, further including a fill hole formed in said constriction, a duct communicating between said electrolyte chamber and said fill hole and a removable cap closing said fill hole.

5. A probe as set forth in claim 2, further including a cavity formed in said constriction, a thermistor disposed in said cavity and connected to contact terminals in said terminal chamber.

6. A cell as set forth in claim 1, wherein said cathode is formed of gold.

7. A cell as set forth in claim 1, wherein said membrane is formed of tetrafluoroethylene.

* * * * *